United States Patent [19]

Kenkare et al.

[11] 4,108,977

[45] *Aug. 22, 1978

[54] METHOD OF PRODUCING IMPROVED ANTIPERSPIRANT COMPOSITION

[75] Inventors: Divaker B. Kenkare, South Plainfield; Durland K. Shumway, Piscataway, both of N.J.

[73] Assignee: Colgate-Palmolive Company, New York, N.Y.

[*] Notice: The portion of the term of this patent subsequent to Sep. 12, 1995, has been disclaimed.

[21] Appl. No.: 557,562

[22] Filed: Mar. 12, 1975

[51] Int. Cl.$^2$ .............................................. A61K 7/38
[52] U.S. Cl. ...................................... 424/46; 424/47; 424/68
[58] Field of Search ............................. 424/47, 68, 46

[56] References Cited

U.S. PATENT DOCUMENTS 3,873,686 3/1975 Beekman ................................ 424/47

FOREIGN PATENT DOCUMENTS 770,007 3/1957 United Kingdom ..................... 424/68
1,347,950 2/1974 United Kingdom ..................... 424/47

Primary Examiner—Dale R. Ore
Attorney, Agent, or Firm—Herbert S. Sylvester; Murray M. Grill; Norman Blumenkopf

[57] ABSTRACT

An improved antiperspirant composition can be prepared by co-spray drying together a mixture of aluminum chloride, aluminum chlorhydrate, and urea. The co-spray drying technique produces an impalpable powder which may be incorporated into an antiperspirant formulation suitable for aerosol application.

11 Claims, No Drawings

METHOD OF PRODUCING IMPROVED ANTIPERSPIRANT COMPOSITION

BACKGROUND OF THE INVENTION

The present invention relates to a method for preparing an improved antiperspirant composition which can be incorporated into an antiperspirant formulation suitable for aerosol application.

Aerosol formulations under pressure have become popular as a convenient form for application of antiperspirant formulations to the skin. Aerosol antiperspirant and deodorant products now occupy a majority of the market for antiperspirant and deodorant products.

An aerosol product which possesses the attractive cosmetic properties and convenience benefits of currently available aerosol deodorant products and which additionally possesses substantial antiperspirant effects without excessive skin irritation would be highly desirable. Since the known inorganic astringent salts possess far greater antiperspirant activity than the organic astringent salts heretofore suggested for aerosol use, the inorganic salts must be used, despite the formulation problems involved, to provide such a product.

Among the most effective astringent inorganic salts are aluminum chloride and aluminum chlorhydrate. Aluminum chlorhydrate, also known as aluminum chlorhydroxide complex or basic aluminum chloride, has an approximate atomic ratio of aluminum to chlorine of 2:1, e.g., 2.1:1 to 1.9:1, and an empirical formula of $Al_2(OH)_5Cl$, existing as a hydrate in solid form.

The efficacy of an antiperspirant composition is largely dependent upon the relative activity of the astringent salt employed therein. However, skin irritation results from the low pH of many conventional antiperspirant formulations. It is known that urea is very effective in reducing skin irritation caused by these formulations without reducing their efficacy. However, the large particle size and hygroscopicity of urea so far has prevented its incorporation into dry aerosol type antiperspirant products.

Accordingly, it is a primary object of this invention to provide a method for making an antiperspirant composition which can be effectively incorporated into an aerosol antiperspirant formulation.

It is a further object of this invention to provide a method of incorporating urea in a "dry" power aerosol antiperspirant formulation in which skin irritation and valve clogging are minimized.

SUMMARY OF THE INVENTION

It has now been discovered that these and other objects are achieved by co-spray drying together urea and solutions of aluminum chloride and aluminum chlorhydrate to form an impalpable powder.

Preferably, an aqueous solution of aluminum chlorhydrate is co-spray dried with an aqueous solution of aluminum chloride and solid urea. In general, the aluminum chloride is used as an aqueous solution of aluminum chloride having the following general composition: Aluminum expressed as aluminum, 5.6-5.8%; Chlorine, 20-23%, and the balance water. The final, dry composition may contain from about 78% to about 92% aluminum chlorhydrate, from about 6% to about 12% aluminum chloride, and from about 1% to about 10% urea. Preferred final dry compositions may contain from about 85% to 90% aluminum chlorhydrate, from about 8% to 12% aluminum chloride, and from about 2% to 7% urea.

DESCRIPTION OF THE PREFERRED EMBODIMENTS

EXAMPLE I

An antiperspirant composition was prepared from the following starting materials:

|  | % by weight |
|---|---|
| Aluminum chlorhydrate aqueous solution (50% $Al_2(OH)_5Cl$, balance water) | 87.7 |
| Aluminum chloride aqueous solution (29% $AlCl_3$, balance water) | 9.8 |
| Urea | 2.5 |

The above ingredients were blended in a glass-lined vessel in the order given with minimal mechanical agitation needed to solubilize the urea. The liquid blend yielded an atomic ratio, on a theoretical basis of Al:Cl of about 1.6:1.

The ingredients were spray dried together in a Komline-Sanderson "Little Giant" spray dryer, which had a drying chamber three feet in diameter with a three foot cylinder height and a 60° conical bottom. Heat was supplied by three direct-fired gas burners. Atomization was accomplished with a two-fluid atomizer.

The liquid mixture can be fed into the spray dryer at any temperature, although the temperature preferably ranges from about 55° F. to about 80° F. The viscosity of the feed is less than 500 cps. and the feed rate can vary from about 50 ml/minute to about 200 ml/minute. The inlet air temperature ranges from about 350° F. to about 410° F., and the outlet air temperature ranges from about 160° F. to about 210° F. The air pressure ranges from about 60 psi to about 100 psi; the feed pressure is less than 10 psi.

Larger amounts of the antiperspirant composition can be prepared in a gas-fired cone-bottom spray dryer having a diameter of twelve feet and a height of ten feet on the straight side. In this instance the inlet air temperature ranges from about 400°–410° F. and the outlet air temperature ranges from about 195°–210° F. The air pressure is about 70 psi, and the feed rate of liquid is approximately 125–150 gallons per hour.

The oven loss of the resulting product as measured at 105° C. for 16 hours indicates a ratio of about 10–12%, and the product is micronized to a particle size of 100% through 325 mesh using a rotor/stator micronizing mill.

EXAMPLES II AND III

The method described in EXAMPLE I can be used to prepare a variety of additional antiperspirant compositions, examples of which are given below. The proportions of starting materials are given in parts by weight:

|  | II | III |
|---|---|---|
| Aluminum chlorhydrate solution of EXAMPLE I | 85 | 80 |
| Aluminum chloride solution of EXAMPLE I | 15 | 20 |
| Urea | 2.6 | 2.6 |

EXAMPLE IV

The method of EXAMPLE I was used to prepare a dry powder having the following analysis expressed as percent by weight:

| | |
|---|---|
| $Al_2(OH)_5Cl$ | 88.93 |
| $AlCl_3$ | 5.93 |
| Urea | 5.14 |
| Al:Cl ratio | 1.61:1 |

All of the above spray-dried powders are micronized to a particle size of 100% through a 325 mesh Tyler Screen utilizing a rotor/stator micronizing mill.

Antiperspirant compositions prepared according to the method of the present invention are particularly well suited for incorporation into aerosol antiperspirant compositions, as valve clogging by the hygroscopic urea and aluminum salts is minimized by co-spray drying the ingredients into an impalpable powder. Antiperspirant formulations can readily be prepared from the antiperspirant compositions of the present invention by adding to the co-spray dried antiperspirant compositions the usual cosmetically acceptable adjuvants and propellants. Typically, a suspending agent is used to keep the antiperspirant composition from agglomerating or settling out and packing tightly at the bottom of the aerosol container. A carrier is added so that the stream issuing from the aerosol container is a moist spray which effectively adheres to the skin rather than a dusty cloud which does not adhere as well. A non-toxic, normally gaseous, liquefied propellant is added to force the antiperspirant formulation out of the container. Minor adjuvants such as antimicrobial compounds and perfumes are optional.

It has been found that antiperspirant compositions prepared according to the method of the present invention are particularly well suited for powder use type antiperspirant formulations, in which case talc or other suitable powder may be added to the formulation.

EXAMPLE V

A powder type aerosol antiperspirant formulation was prepared including the following ingredients:

| | | % by weight |
|---|---|---|
| blend | Aluminum chlorhydrate | 5.62 |
| | Aluminum chloride | 0.38 |
| | Urea | 0.32 |
| | Isopropyl palmitate | 6.41 |
| | Bentone 38* | 0.29 |
| | Propylene carbonate | 0.10 |
| | Zinc stearate | 0.15 |
| | Perfume | 0.20 |
| | Propellant (18% Trichloromonofluoromethane (Freon 11), 10% Dichlorodifluoromethane (Freon 12), 50% Dichlorotetrafluoroethane (Freon 114), 22% n-butane) | 86.53 |

*National Lead Co. organically modified Montmorillonite clay(quaternium 18 hectorite)

A sweat test was conducted to determine the efficacy of the antiperspirant formulation. Six weeks prior to the test the panelists used a mild deodorant having no antiperspirant activity in order to equilibrate the sweat activity of their armpits. During a one week control period during which the panelists used only a mild deodorant, the panelists were subjected to an emotional challenge to produce sweat, and the sweat was collected on sponges placed under the arms. This was done four times during a one week period to obtain an average of the amount of sweat under each arm.

To test the antiperspirant formulation, each panelist used the product antiperspirant under one arm, and a mild deodorant under the other arm. Each product was applied daily, and the sweat reduction was measured 24 hours after the seventh, eleventh, thirteenth, and fourteenth days of application. After the sweat is measured, the ratio of the sweat of the test underarm to the sweat of the control underarm is compared to the ratio of sweat under each underarm in the control period in order to measure sweat reduction.

The antiperspirant formulation of EXAMPLE V was tested for sweat reduction, and the results tabulated below:

| Days of Product Use | Sweat Reduction |
|---|---|
| 7 | 45.6% |
| 11 | 52.0% |
| 13 | 50.4% |
| 14 | 55.5% |

EXAMPLE VI

A standard aerosol antiperspirant formulation was prepared from the following ingredients:

| | % by weight |
|---|---|
| Aluminum chlorhydrate | 6.50 |
| Isopropyl myristate | 8.70 |
| Colloidal Silica (Cab-O-Sil M5) | 0.43 |
| Perfume | 0.20 |
| Propellant (60% Freon 11, 40% Freon 12) | 84.37 |

This conventional antiperspirant formulation was tested for sweat reduction as described supra, and the results tabulated below:

| Days of Product Use | Sweat Reduction |
|---|---|
| 7 | 29.9% |
| 11 | 35.0% |
| 13 | 34.4% |
| 14 | 28.6% |

Although the additions in the formulation of EXAMPLE VI are not exactly the same as those in EXAMPLE V, it is obvious that the formulation of EXAMPLE V, using an antiperspirant composition co-spray dried according to the present invention, gives superior sweat reduction when compared with a typical aerosol antiperspirant formulation.

What is claimed is:

1. A method for making an antiperspirant composition comprising co-spray drying together a liquid mixture of (a), urea, and (b) an aqueous solution of aluminum chloride and (c) aluminum chlorhydrate to form an impalpable powder containing about 1–10% of component (a), about 6–12% of component (b) and about 78–92% of component (c).

2. The method of claim 1 wherein the powder is micronized to a particle size of about 325 mesh.

3. The method of claim 1 wherein the powder contains about 85% to about 90% by weight aluminum chlorhydrate, about 8% to about 12% by weight aluminum chloride and about 2% to about 7% by weight urea.

4. The method of claim 1 wherein the urea is present in the amount of about 2.6 parts by weight, the aluminum chlorhydrate solution is present in an amount of about 90 parts by weight of 50% aqueous solution of aluminum chlorhydrate, and the aluminum chloride is present in an amount of about 10 parts by weight of an aqueous solution of aluminum chloride containing about 29% aluminum chloride.

5. A method for incorporating urea into a dry aerosol antiperspirant composition comprising co-spray drying the urea with an aqueous solution of a mixture of aluminum chloride and aluminum chlorhydrate, reducing the particle size of the resulting powder so that it passes through a 325 mesh screen and filling said powder into an aerosol container together with propellant.

6. The method as defined in claim 1 wherein component (b) has about 5.6–5.8% aluminum, about 20–23% chlorine and the balance water.

7. The method as defined in claim 1 wherein said components are blended together to solubliize the urea with minimum mechanical agitation prior to spray drying.

8. The method as defined in claim 1 wherein said powder has an theoretical atomic ratio of Al:Cl of about 1.6:1.

9. The method as defined in claim 1 wherein said liquid is fed into a spray dryer at a temperature of about 55° F to 80° F.

10. The method as defined in claim 1 wherein said liquid has a viscosity of less than about 500 cps.

11. The method as defined in claim 1 wherein said liquid is fed into a spray dryer at a rate of about 50 ml/min — 200 ml/min.

* * * * *